(12) United States Patent
Crawford et al.

(10) Patent No.: US 7,517,564 B2
(45) Date of Patent: Apr. 14, 2009

(54) METHOD FOR IDENTIFYING ARTICLES AND PROCESS FOR MAINTAINING SECURITY

(75) Inventors: Michael Karl Crawford, Glen Mills, PA (US); Kurt Richard Mikeska, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/954,253

(22) Filed: Dec. 12, 2007

(65) Prior Publication Data

US 2008/0206486 A1    Aug. 28, 2008

Related U.S. Application Data

(60) Provisional application No. 60/876,321, filed on Dec. 21, 2006.

(51) Int. Cl.
*B05D 3/06* (2006.01)
(52) U.S. Cl. ............... 427/558; 427/98.4; 427/99.4; 427/157; 427/594; 313/483; 428/41.5; 356/230; 423/263; 423/258; 423/274
(58) Field of Classification Search ............ 427/558; 423/263; 313/483; 428/41.5
See application file for complete search history.

(56) References Cited

U.S. PATENT DOCUMENTS

| 6,861,012 B2 | 3/2005 | Gardner et al. | |
| 2002/0027412 A1 | 3/2002 | Hisashi et al. | |
| 2003/0032192 A1 | 2/2003 | Haubold | |
| 2005/0068395 A1* | 3/2005 | Haubold et al. | 347/100 |
| 2005/0143249 A1 | 6/2005 | Ross et al. | |

(Continued)

FOREIGN PATENT DOCUMENTS

EP    0 147 252 A1    7/1985

(Continued)

OTHER PUBLICATIONS

Martin et al., Atomic Energy Levels—The Rare-Earth Elements, U.S. Department of Commerce, National Bureau of Standards, 1978, (Book not Included).

(Continued)

*Primary Examiner*—Duy-Vu Deo
*Assistant Examiner*—Maki Angadi

(57) ABSTRACT

The invention is directed to a method by exposing at least a portion of a luminescent coating disposed on a surface of an article to ultraviolet light at one or more preselected wavelengths causing said luminescent coating to exhibit a luminescence spectrum, the luminescence spectrum exhibiting a plurality of intensity peaks that have been predetermined to create a standard; determining the intensity of at least two peaks in the luminescence spectrum of the coating; determining a peak intensity ratio of the at least two peaks; comparing the peak intensity ratio determined with the standard; and, classifying the article according to whether or not the peak intensity ratio does or does not match the standard; wherein the luminescent coating is a particulate luminescent composition comprising a rare earth doped fluoride represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a, b, and c are not equal to zero; the particulate luminescent composition exhibiting a luminescence spectrum having a plurality of intensity peaks at characteristic wavelengths.

16 Claims, 1 Drawing Sheet

U.S. PATENT DOCUMENTS

2007/0108413 A1  5/2007  Chi et al.
2008/0025896 A1  1/2008  Chi et al.

FOREIGN PATENT DOCUMENTS

EP       1 728 763 A2    12/2006
EP       1 884 553 A2     2/2008
WO    WO 03/052025 A1    6/2003

OTHER PUBLICATIONS

Sarma et al., Ionic Conductivity of CaF2-SrF2 Mixed Crystals, Solid State Ionics, 1990, vol. 42:227-232.

Federov et al., Crystallization of a Solid Solution With Fluorite Structure in the CaF2-SrF2-NdF3 System in the Vicinity of the Saddle Point on the Liquidus Surface, Dolady Akademi Nauk, 1999, vol. 369:217-219.

K. Kawano et al., Photoluminescence of Eu2+ Ion Doped Into CA1-Srf2 Mixed Crystlas, Japanese Journal of Applied Physics, 1990, vol. 29:319-321.

F. Wang et al., Synthesis and Luminescence Behavior of Eu3+ doped CaF2 Nanoparticles, Solid State Communications, 2005, vol. 133:775-779.

E. Faulques et al., Synthesis, Fabrication, and Photoluminescence of CaF2 Doped With Rare Earth Ions, Journal of Fluorescence, 1998, vol. 8:283-287.

Anonymous: Influence of Oxide Concentration on the Image Storage Efficiency of BaFBr Phosphor Materials, Research Disclosure 33641, 1992, vol. 336, Issue No. 41, Mason Publications.

* cited by examiner

METHOD FOR IDENTIFYING ARTICLES AND PROCESS FOR MAINTAINING SECURITY

FIELD OF THE INVENTION

The present invention is directed to a method for identifying articles, for the purpose of thwarting counterfeiting, by marking the articles with luminescent particles comprising a rare-earth doped solid state solution of alkaline earth fluorides.

BACKGROUND OF THE INVENTION

Luminescent rare-earth doped alkaline-earth fluorides have long been known, and have been employed for numerous purposes such as scintillation detectors and laser materials. $CaF_2$ doped with such rare-earth species as $Eu^{+3}$, $Er^{+3}$, $Tb^{+3}$ are well-known compositions. It is well-known that a rare-earth doped alkaline earth fluoride will exhibit luminescence when exposed to ultraviolet light.

Each rare-earth element when incorporated into an alkaline earth host lattice such as $CaF_2$ exhibits a characteristic excitation spectrum; see, for example, FIG. 1 (101), and a characteristic emission or luminescence spectrum that depends upon the excitation wavelength employed; see, for example, FIG. 1 (102). The excitation spectrum is determined by monitoring the luminescence intensity at one wavelength while the specimen is illuminated over a range of wavelengths. The luminescence spectrum is determined by illuminating the specimen at a single wavelength corresponding to a peak in the excitation spectrum and determining the luminescence spectrum by scanning a detector over a range of wavelengths.

As shown in the figures, each such spectrum consists of a plurality of peaks at different wavelengths of light. The wavelengths at which the peaks occur are characteristic of each rare-earth element. No two rare-earth elements exhibit the same excitation or emission spectra; that is, the peaks in their spectra do not in general arise at the same wavelengths. To obtain luminescence, the rare-earth element must be excited by a light source that emits light at a wavelength corresponding to the location of one of the peaks in the excitation spectrum thereof. In general, the peaks in any one spectrum of rare-earth elements differ from one another in height or intensity, these differences in intensity being characteristic of the rare-earth element under particular conditions of measurement. These and related matters are all well-documented in the art. See for example, Martin et al., *Atomic Energy Levels—the Rare-Earth Elements*, U.S. Department of Commerce, National Bureau of Standards (1978).

Haubold et al., U.S. Published Patent Application 2003/0032192 discloses the use of doped luminescent inorganic compounds for marking goods, such as in use as so-called anti-theft or anti-counterfeiting security markers. Use of rare-earth doped alkaline earth fluorides is not disclosed. Haubold et al., WO 03/052025 specifically discloses printing using the compositions disclosed in Haubold et al., op.cit. No details are provided. Rare-earth doped alkaline earth compositions are not disclosed.

Gardner et al., U.S. Pat. No. 6,861,012, discloses use of phosphorus-based inorganic chelates that are "cropped to" polymer particles employed in ink jet printing inks to provide UV-activated luminescence for marking goods. There is no disclosure of rare-earth doped alkaline earth fluoride compositions.

Ross et al., U.S. Published Patent Application 2005/0143249, disclose the use of rare-earth doped glasses for use in security labels. Disclosed are mixtures of rare-earth doped glasses that give rise to variations in relative emission intensity at pre-selected wavelengths.

Federov et al., Doklady Akademii Nauk. 369(2):217-219, 1999, discloses solid solutions consisting of a series of 10 mm diameter and 50 mm long single crystals of $(Ca_{1-y}Sr_y)_{1-x}Nd_xF_{2+x}$ grown by the Bridgman-Stockbarger method by crystallization from the melt.

Security marks known in the art generally lack sufficient complexity or encryption to make them difficult to counterfeit themselves. The present invention provides a family of novel rare-earth-doped alkaline earth fluorides, and a process for preparing them, that are characterized by continuously variable luminescence peak intensity ratios, making it extraordinarily difficult to counterfeit security marks having these compositions.

SUMMARY OF THE INVENTION

The present invention provides a method comprising exposing at least a portion of a luminescent coating disposed on a surface of an article to ultraviolet light at one or more preselected wavelengths, causing said luminescent coating to exhibit a luminescence spectrum the luminescence spectrum exhibiting a plurality of intensity peaks that have been pre-determined to create a standard; determining the intensity of at least two peaks in the luminescence spectrum of the coating; determining a peak intensity ratio of at least two peaks; comparing the peak intensity ratio thereby determined with the predetermined standard; and, classifying the article according to whether or not the peak intensity ratio does or does not match the standard; wherein the luminescent coating comprises a particulate luminescent composition comprising a rare-earth-doped solid-state solution of alkaline earth fluorides represented by the chemical formula

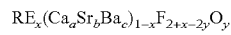
$$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a,b, and c are not equal to zero; the particulate luminescent composition exhibiting a luminescence spectrum having a plurality of intensity peaks at characteristic wavelengths.

Further provided in the present invention is a method having, within a first time period, a coater causing to be disposed upon the surface of a first plurality of articles, a first luminescent coating, thereby producing a first plurality of coated articles; and, within a second time period, the coater causing to be disposed upon the surface of a second plurality of articles, a second luminescent coating, thereby producing a second plurality of coated articles; a classifier causing to be exposed at least a portion of one or more of the first or second plurality of coated articles to ultraviolet light at one or more preselected wavelengths thereby causing the coating to exhibit, respectively a first or second luminescence spectrum, each said first or second luminescence spectrum exhibiting a plurality of intensity peaks the wavelengths of the peaks having been predetermined using light comprising the preselected wavelength or wavelengths to create a first standard corresponding to the first plurality of coated articles and a second standard corresponding to the second plurality of coated articles; determining the peak intensity ratio of at least two intensity peaks in the first or second luminescence spectrum of the first or second coating; comparing the peak intensity ratio so determined with, respectively, the first or second standard depending upon whether the coated article is from the first or second plurality of coated articles; and, classifying the article according to whether or not the peak intensity ratio does or does not match the first or second standard, respectively; each said coating comprising a particulate luminescent composition, the particulate luminescent composition comprising a rare-earth-doped solid-state solution of alkaline earth fluorides represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a, b, and c are not equal to zero; the particulate luminescent composition exhibiting a luminescence spectrum having a plurality of intensity peaks at characteristic wavelengths.

DETAILED DESCRIPTION

Figure 1:
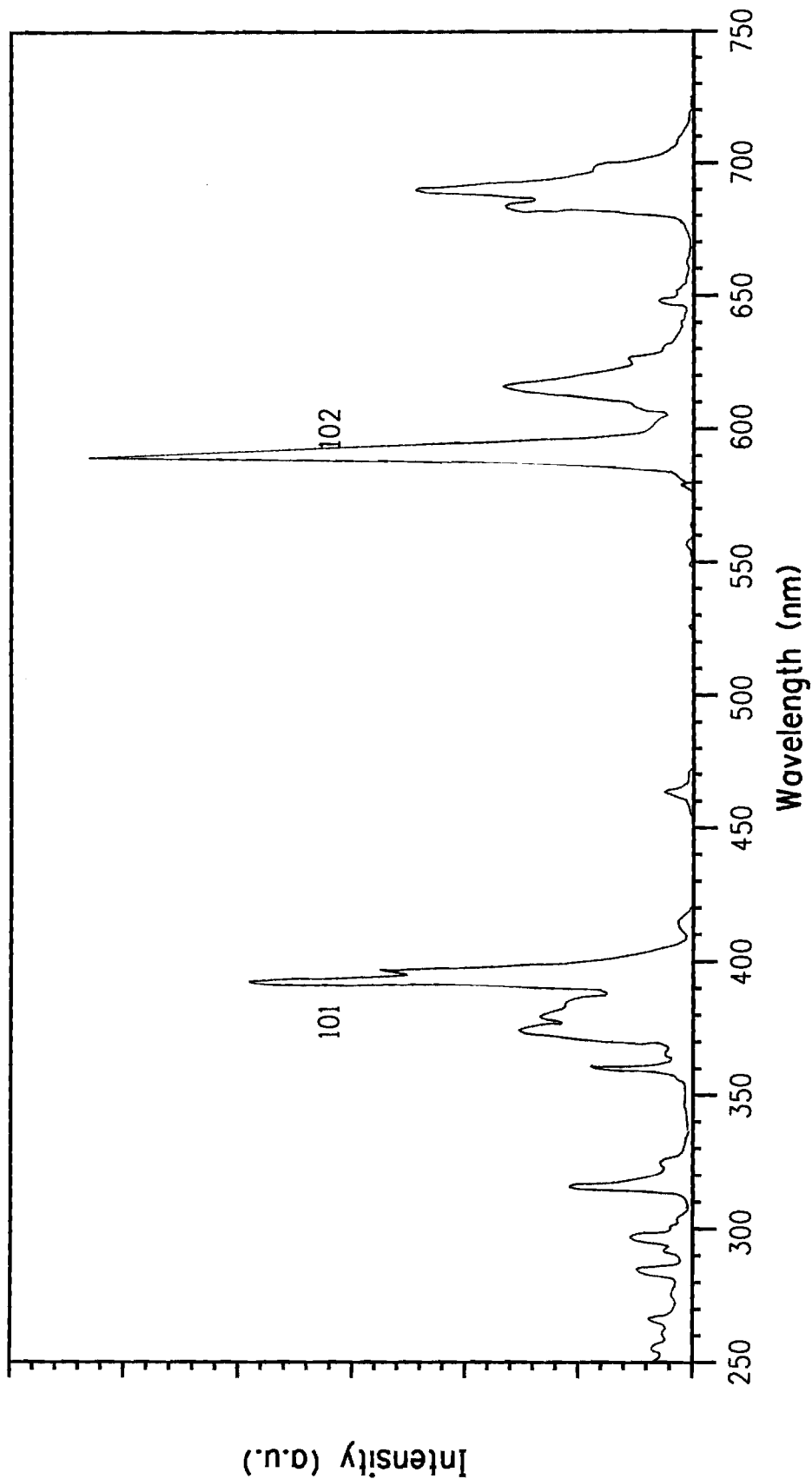
FIG. 1 is an excitation spectrum of $Eu_{0.05}Ca_{0.95}F_{2.05-2y}O_y$ observed at 591 nm and a luminescence spectrum of $Eu_{0.05}Ca_{0.95}F_{2.05-2y}O_y$ excited at 394 nm.

For the purposes of the present invention, the term "classifying" shall be understood to refer to some action undertaken to segregate the coated articles that match the standard from those that do not. Classification can involve sorting into separate boxes, bins, and the like, or could involve simply placing a further marking of some sort on the article to indicate conformity or non-conformity with the standard. In another embodiment classification may simply be a list that can be kept by hand or on a computer memory. The term "classifier" shall be understood to refer to any agent that can determine whether or not the measured peak intensity ration corresponds to the standard, and can cause the act of classification to occur. The classifier may be a human being, but need not be. The classifier can also be a robot or other device that performs the necessary functions.

As the present invention is employed, the manufacturer or distributor of an article acts as the "coater" causing the surface of an article to be marked according to the methods herein disclosed in order to provide positive identification or confirmation of the authenticity of the article so marked. In the sense employed herein, the term "coater" may comprise one or more human beings, corporate entities, and/or robotic devices. The "coater" may refer both to the corporate entity and to a plurality of human beings (for example, shift workers) under the auspices of which corporate entity physically apply the luminescent coating to the surface of the article. "Coater" encompasses the means by which the coating is applied, as well as the means by which the standard is determined. According to the present invention, it is the coater that determines the luminescence standard, and communicates that standard to the "classifier."

The standard includes information regarding the exposure wavelength, the location of the peaks in the luminescence spectrum, and the peak intensity ratio. This information is communicated from the "coater" to the "classifier" so that the classifier is able to distinguish conforming (authentic) from non-conforming (counterfeit) articles.

In an embodiment, the coated article is transferred, by shipping, to a recipient, typically a customer or a jobber. The recipient then makes inquiry of the coated article employing a light source that emits at the preselected wavelengths, and a detector that enables determination of peak intensity ratio of the selected luminescence peaks.

The present invention provides a method comprising exposing at least a portion of the coated surface of an article having a surface having a luminescent coating comprising a particulate luminescent composition to ultraviolet light at one or more preselected wavelengths thereby causing the coating to luminance, the luminescence spectrum of the coating exhibiting a plurality of intensity peaks that have been predetermined using light comprising the preselected wavelength or wavelengths to create a standard; determining the peak intensity ratio of at least two peaks in the luminescence spectrum of the coating; comparing the peak intensity ratio so determined with the standard; and, classifying the article according to whether or not the peak intensity ratio does or does not match the standard; the particulate luminescent composition comprising a rare-earth-doped solid-state solution of alkaline earth fluorides represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a,b, and c are not equal to zero; the particulate luminescent composition exhibiting a luminescence spectrum having a plurality of intensity peaks at characteristic wavelengths.

In a further embodiment of the invention, at least one pair of the intensity peaks in the luminescence spectrum of the particulate luminescent composition exhibits an intensity ratio with respect to one another that differs by at least 5% from the corresponding intensity ratio of the corresponding reference composition. In another embodiment, it differs by a least 10%.

The rare-earth doped solid state solution of alkaline earth fluorides suitable for use herein has many embodiments that differ from one another, inter alia, by virtue of the particular rare-earth, and the particular alkaline earth cations incorporated therein, as well as by the relative amounts thereof, that is, by the values of x, a, b, and c. To each said rare-earth doped solid state solution of alkaline earth fluorides suitable for use herein there corresponds a so-called "reference composition." The reference composition is a solid state solution consisting of the same rare-earth and alkaline earths in the same relative amounts as that suitable or use herein to which it corresponds; that is, RE, x, a, b, and c are the same as in that of the rare-earth doped solid state solution of alkaline earth fluorides suitable for use herein to which the reference composition corresponds. However, unlike the rare-earth doped solid state solution of alkaline earth fluorides suitable for use herein, that can be prepared according to the process described infra, the reference composition is prepared by crystallization from the melt in the manner of Federov, op. cit. Each rare-earth doped solid state solution of alkaline earth fluorides suitable for use herein, and each reference composition corresponding thereto, is characterized by a luminescence spectrum having a plurality of luminescence peaks at characteristic wavelengths. Any pair of said plurality of luminescence peaks is characterized by the ratio of the intensities (or heights) thereof. According to the present invention, for each rare-earth doped solid state solution of alkaline earth fluorides suitable for use herein, there is at least one pair of said plurality of peaks whereof the ratio of said intensities (or intensity ratio) differs by at least 5% from the intensity ratio of peaks at the same wavelengths in the luminescence spectrum of the corresponding reference composition.

In order to provide enhanced security, the coater employs in a first period of time a first luminescent coating with which to mark the manufactured articles, and during a second period of time, employs a second luminescent coating, different from the first luminescent coating. In such case, the coater informs the classifier of the change from the first standard to the second standard. Both the luminescent coatings comprise a particulate luminescent composition, the particulate luminescent composition comprising a rare-earth-doped solid-state solution of alkaline earth fluorides represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, a+b+c=1, with the proviso at least two of a,b, and c are not equal to zero; the particulate luminescent composition exhibiting a luminescence spectrum having a plurality of intensity peaks at characteristic wavelengths.

In a further embodiment, at least one pair of the intensity peaks in the luminescence spectrum of the particulate luminescent composition exhibits an intensity ratio with respect to one another that differs by at least 5% from the corresponding intensity ratio of the corresponding reference composition.

For the purpose of the present invention the term "solid state solution" is employed to refer to a composition such as but not limited to $Sr/CaF_2$:$EuF_3$, that forms a single crystalline phase as indicated by x-ray diffraction (XRD) analysis whereas a simple mixture of, e.g., a $SrF_2$:$EuF_3$ and a $CaF_2$:$EuF_3$ is shown by XRD to consist of multiple crystalline phases.

The rare-earth doped solid state solutions of alkaline earth fluorides suitable for use in the present invention may conveniently be prepared according to the precipitation process and, if desired, the heating process described, infra. However, the composition is not limited in scope to any particular means of preparation for the rare-earth doped solid state solutions of alkaline earth fluorides. For the purposes of the present invention, the process by which the composition is synthesized shall be known as the "precipitation process." Any embodiment of the rare-earth doped composition suitable for use herein that has not been exposed to a temperature above 100° C. shall be referred to as an "as-precipitated" embodiment regardless of whether that embodiment was actually prepared by precipitation.

The particulate luminescent composition suitable for use in the present invention comprises the rare-earth doped solid state solution of alkaline earth fluorides suitable for use herein. The rare-earth doped solid state solution of alkaline earth fluorides suitable for use herein is itself particulate in nature as well as luminescent. However, as described infra, the particulate luminescent composition suitable for use in the present invention may include additional materials.

The rare-earths suitable for the practice of the invention include all the members of the Lanthanide series in the periodic table of the elements with the exception of promethium and lutetium. The rare-earth elements are all in the +3-valent state. Eu+3, Er+3, and Tb+3 are preferred.

In a further embodiment $0.01 \leq x \leq 0.10$.

In another embodiment, one of a, b, or c=0. In a still further embodiment, a=0.01 to 0.99, b=0.99 to 0.01, and c=0. In a further embodiment, a=0.25 to 0.75 and b=0.75 to 0.25, while c=0.

In a further embodiment, RE is Eu+3, $Er^{+3}$, or $Tb^{+3}$, $0.01 \leq x \leq 0.10$, a=0.01 to 0.99, b=0.99 to 0.01, and c=0, In a still further embodiment $0.02 \leq x \leq 0.10$.

Each rare-earth doped solid state solution of alkaline earth fluorides is characterized by a luminescence spectrum exhibiting a plurality of intensity peaks at specific wavelengths.

The particulate luminescent composition suitable for use in the present invention is not limited to any particular method by which it is prepared. One method for preparing the rare-earth doped solid state solution of alkaline earth fluorides suitable for use herein is a process comprising combining an aqueous solution of an ammonium fluoride with one or more aqueous solutions of the salts of at least two alkaline earth metals, and an aqueous solution of a salt comprising a 3-valent rare earth metal cation, the amount of the rare-earth metal cation being in the range of 0.5 to 20 mol-% of the molar concentration of the total alkaline earth metal cation content, thereby forming a reaction mixture from which is formed a precipitate of a rare-earth doped solid state solution of alkaline earth fluorides represented by the formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, a+b+c=1, with the proviso at least two of a, b, and c are not equal to zero; the rare-earth doped multi-valent metal fluoride being characterized by an aqueous solubility of less than 0.1 g/100 g of water.

The reaction in aqueous solution of the soluble fluoride with the soluble alkaline earth salts and rare earth salt is very rapid. Precipitation occurs so quickly in the process of the invention that there is little time for crystal growth after nucleation, except in highly dilute solution.

The particles so produced comprise a crystalline or semi-crystalline host material and a dopant. The host material is a solid state solution of at least two alkaline earth fluorides characterized by an aqueous solubility of less than 0.1 g/100 g of water. The dopant is a three-valent rare-earth cation which occupies specific lattice sites in the crystalline structure of the host material.

In the process for preparing the rare-earth doped solid state solution of alkaline earth fluorides suitable for use herein ammonium fluoride is combined with one or more aqueous solutions of the salts of at least two alkaline earth metals, and an aqueous solution of a rare earth metal salt. The aqueous solubility of the resulting rare-earth doped solid state solution of two or more alkaline earth fluorides is less than 0.1 g/100 g at room temperature.

The term "rare-earth" refers to the members of the Lanthanide Series in the periodic table, namely La, Ce, Pr, Nd, Sm, Eu, Gd, Tb, Dy, Ho, Er, Tm, and Yb.

Preferred anions for the soluble alkaline earth metal salt include chloride, nitrate, sulphate, hydroxide, acetate, carbonates, phosphates, bromides, and hydrates thereof.

The precipitation process can be employed to make both nano-sized particles and micro-sized particles, depending upon the reaction conditions. For the purpose of the present invention, the term "nano-sized" shall be understood to refer to a batch of particles of which fewer than 50%, preferably fewer than 90%, of the particles by weight are trapped in a 200 nm filter. It has been found in the practice of the invention that a 0.2 micrometer Zapcap-CR chemically resistant bottle top filter available from Schleicher & Schueel Microscience, is satisfactory for this determination.

For the purpose of the present invention, the term micro-sized shall be understood to refer to a batch of particles of which at least 50%, preferably at least 90%, of the particles by weight are trapped in a 500 nm filter. Particles said to be micro-sized shall be further characterized in that fewer than 50%, preferably fewer than 90%, of the particles by weight are trapped in a 200 micrometer filter.

Soluble salt starting materials need only be soluble enough to form aqueous solutions of the desired concentrations for the purposes of the present invention. A salt is, for the purposes herein, said to be aqueously soluble if a solution of the desired concentration can be formed from it.

Three processes are involved in the precipitation of a solid product from a homogenous reaction solution. (1) chemical reactions that produce supersaturation, (2) nucleation of particles and (3) and growth of particles. For fast reactions, such as occur herein, small particles are produced when there is a localized high concentration of the crystallizing species in solution and high supersaturation, which results in high nucleation rates, high nuclei densities, and low growth rates. Large particles are produced by reducing the local solution supersaturation, which decreases the nucleation rate and increases the growth rate.

From a processing standpoint, final particle size can be influenced by controlling initial reactant concentrations, crystallizing species concentration (supersaturation) and mixing conditions.

It is observed that increasing the concentration of the rare-earth dopant decreases the size of the particle produced. As a general guideline, preparation of nano-scale particles is beneficially accomplished by employing reactant concentrations of >0.01N, preferably in the range of 0.1N to 0.8N, while preparation of micro-scale particles is beneficially accomplished by employing reactant concentrations of <0.01N. Nano-scale particles may beneficially be prepared by direct mixing of the precursor solutions as in a T-mixer or by some other form of direct mixing. In these cases the local supersaturation is high resulting in high nucleation rates, low growth rates and nano-scale particles. While micro-scale particles can also be prepared by direct mixing of highly dilute solutions, it is more convenient to combine ca. 1N solutions of the reactants in a well-stirred aqueous bath that provides a dilution factor of ca. 100-200 times—for example combining 1 liter of 2N of each alkaline earth chloride, and the appropriate amount of $EuCl_3$, and $NH_4F$ in 120 liters of well-stirred water has been found to be satisfactory for preparing micro-scale particles. In these cases the local supersaturation is low resulting in low nucleation rates, high growth rates and micron size scale particles. It is important to stir the reaction vessel to effectively reduced the local supersaturation.

For the production of nano-scale particles, it is convenient to combine the reactants in a T-mixer on a continuous or semi-continuous basis. Reaction is essentially instantaneous, with nano-particulate precipitate forming in the output leg of the T as the reaction stream flows into the collector vessel. For production of micro-scale particles, the highly diluted ingredients, with concentrations of <0.01N, may need to be allowed to stand and react while being stirred for about 30 minutes. The pH of the reaction mixture is preferably maintained close to neutral, but a pH range from about 1 to 11 is acceptable.

Following reaction, the product may be conveniently separated by centrifugation and decanting of the supernatant liquid. The isolated "wet cake" so produced may then be redispersed in water (or organic solvents by a solvent exchange process) by mixing with liquid and subjecting the mixture to ultrasonic agitation for a period of 5-30 minutes. The dispersed particles are then in form well-suited to use in coatings and the like. For dispersion in non-polar solvents, it may be required to combine the particles produced with surfactants, as taught in the art.

Other suitable methods of separating the precipitate include ion exchange, dialysis and electrodialysis substantially eliminates all salts produced in the process. Further methods, to separate and concentrate the sample, include evaporation of water, centrifugation, ultrafiltration, electrodecantation. A preferred procedure is to employ ion exchange resins to remove soluble salt residues followed by evaporation to concentrate the colloidal sol produced.

It is preferred that the particles so prepared be subject to water washing in order to remove any residual water soluble starting materials. Dispersing in water followed by centrifugation is one effective method.

The resulting particles exhibit luminescence when subject to suitable optical excitation. It has been found that thermal post-treatment to about 200° C. to 1000° C. may alter certain luminescent properties, in some cases, enhancing luminosity or lifetime.

When a composition comprising a rare-earth-doped solid-state solution of alkaline earth fluorides represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a, b, and c are not equal to zero, that has been synthesized at a temperature below about 100° C., is heated in the presence of oxygen in the temperature range from 200-1000° C., it gives rise to a family of novel rare-earth-doped alkaline earth fluorides that differ from one another in their luminescence peak intensity ratios. Each member of any said family exhibits a luminescence spectrum having a plurality of luminescence peaks at characteristic wavelengths. At least one pair of said luminescence peaks exhibits an intensity ratio that differs by at least 5% from the corresponding intensity ratio of the corresponding reference composition, described supra.

It has been observed that upon heating a rare-earth doped solid state solution of alkaline earth fluorides suitable for use herein to a temperature in the range of 200-1000° C., the value of y is observed to increase.

Every member of each such family of compositions exhibits a luminescence spectrum having a plurality of luminescence peaks at characteristic wavelengths. For each family of compositions according to the present invention, there exists at least one pair of the peaks, the relative intensities of which changes depending upon the temperature/time profile to which the as-precipitated composition, described supra, is subject. The heated compositions are characterized by at least one peak intensity ratio that differs by at least 5% from the corresponding peak intensity ratio of the corresponding reference composition.

For the purposes of the present invention, a family of compositions is one in which all members thereof have the same rare-earth element at the same concentration, x, the same alkaline earth elements at the same concentrations, fluorine and oxygen, and wherein members are usually differentiated from one another by the value of y as well as by the relative peak intensity ratio of at least one pair of luminescence peaks.

Suitable means for heating include but are not limited to pressure vessel heating of an aqueous dispersion (so-called hydrothermal heating), electrical resistance furnaces, oil baths, electrically heated crucibles: liquid metal baths; lasers, radio frequency induction furnaces, microwave cavities, gas fired furnaces, oil fired furnaces, solar furnaces. Preferred is an electrical resistance furnace. Typically, when heated in a bath, the as-synthesized powder is sealed in a pressure vessel of sufficient volume to leave a head-space comprising oxygen followed by immersion of the heated tube into the heating bath. When the as-synthesized powder is subject to oven or furnace heating it can be heated in an open crucible.

It has been found satisfactory to heat a rare-earth doped solid state solution of alkaline earth fluorides suitable for use herein gradually to the desired final temperature such as by placing the specimen to be heated into a furnace at room temperature, and then heating to the desired end-point at a rate of 2-10° C./minute, preferably 4-6° C./min.

Heating is effected in the presence of oxygen. There are many potential sources for the oxygen. Heating can be effected in the air, or in an oxygen atmosphere. It is also possible for oxygen to be devolved from species employed or derived from the synthesis environment such as nitrates or hydroxyls. It is believed that even small amounts of oxygen contamination can be sufficient to effect the process.

It is found that the particles of starting material undergo some degree of sintering or agglomeration during heating, particularly at the higher temperatures in the temperature range. Depending upon the particular exigencies of the end use intended, it can be desirable to subject the product of the process to a means for comminution to smaller size. So called media milling is one such method for reducing and/or homogenizing the particle size. Numerous other methods are known in the art.

The rare-earth-doped solid state solutions of alkaline earth fluorides prepared supra can be combined with other ingredients to form compositions suitable for use as coatings or inks. In one embodiment, a rare-earth doped solid state solution of alkaline earth fluorides suitable for use herein is incorporated into an ink composition suitable for printing. In another embodiment, the rare-earth doped solid state solution of alkaline earth fluorides suitable for use herein is incorporated into a paint composition which can be applied by any method known in the art including by brushing, rolling, or spraying.

Numerous chemical formulations are known in the art for preparing inks, paints, and other coating compositions. Every such composition in the art that contains inorganic pigments in particulate form can be employed to formulate an ink, paint, or other coating composition with the particulate luminescent composition serving as the pigment. The rare-earth doped solid state solution of alkaline earth fluorides suitable for use herein may serve as the only pigment, or it may be combined with other pigments and particulate matter such as is known in the art of inks and coatings.

In one formulation, an embodiment of the rare-earth doped solid state solution of alkaline earth fluorides suitable for use herein is incorporated into an ink or coating with no other pigment, thereby resulting in a luminescent coating that after application to the surface of an article is largely invisible to the eye until subject to UV excitation of luminescence.

For the purposes of the present invention, the term "carrier matrix" refers to a continuous medium within which the particulate luminescent composition is dispersed. The carrier matrix can comprise a liquid, a polymer or both.

An ink or coating may be formed by combining a liquid carrier matrix and a particulate luminescent composition dispersed therein, the particulate luminescent composition comprising a rare-earth-doped solid-state solution of alkaline earth fluorides represented by the chemical formula

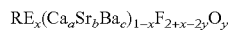

wherein RE represents a three-valent rare-earth element, $0.005 \leq x \leq 0.20$, and $0 \leq y \leq 0.2$, $a+b+c=1$, with the proviso at least two of a,b, and c are not equal to zero; the particulate luminescent composition exhibiting a luminescence spectrum having a plurality of intensity peaks at characteristic wavelengths.

In a further embodiment thereof, the carrier matrix further comprises a polymer. In a still further embodiment thereof, the polymer is dissolved in the liquid; that is, the carrier matrix is a polymer solution.

A composition can be prepared in the form of a dried coating comprising a polymer binder and the particulate luminescent composition dispersed therein the particulate luminescent composition comprising a rare-earth-doped solid-state solution of alkaline earth fluorides represented by the chemical formula

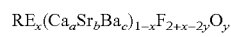

wherein RE represents a three-valent rare-earth element, $0.005 \leq x \leq 0.20$, and $0 \leq y \leq 0.2$, $a+b+c=1$, with the proviso at least two of a,b, and c are not equal to zero; the particulate luminescent composition exhibiting a luminescence spectrum having a plurality of intensity peaks at characteristic wavelengths.

At least one pair of the intensity peaks in the luminescence spectrum of the particulate luminescent compound exhibits an intensity ratio with respect to one another that differs by at least 5% from the corresponding intensity ratio of the corresponding reference composition.

Additional ingredients such as electrolytes, humectants, and other additives also can be present without substantively altering the operability of the invention.

In one embodiment of the particulate luminescent composition, RE is $Eu^{+3}$. In another embodiment, RE is $Tb^{+3}$. In still another embodiment, RE is $Er^{+3}$. In one embodiment of the composition of the invention, a=0, in another embodiment, b=0, and in a third embodiment, c=0. Preferably c=0. In one embodiment of the composition of the invention $0.01 \leq x \leq 0.10$. More specifically, in one embodiment x=0.02. In another embodiment of the composition of the present invention, x=0.05. In still another embodiment x=0.10.

The specific wavelengths of the peaks from which the at least one peak intensity ratio is determined for any particular particulate luminescent composition depend upon the specific rare-earth element employed, and to a lesser degree to the host lattice. However, all the particulate luminescent compositions exhibit the same differentiating characteristic regarding peak intensity ratio changes.

The coating useful in the practice of the present invention can be of any form. It can be in the form of a pattern such as printed text or other images, or it can be a coating of uniform thickness and appearance.

Suitable carrier liquids include but are not limited to water, alkanes such as hexane; alcohols; aldehydes; ketones; ethers, such as dipropylene glycol monomethyl ether; esters, such as ethyl acetate, propyl acetate, or dipropylene glycol monomethyl ether acetate; nitrites, amides, aromatics such as toluene; and mixtures thereof. Water and alcohols are preferred. In one embodiment, methanol, ethanol, propanols, butanols, or mixtures thereof are employed. In another embodiment, water is employed. In a further embodiment, a mixture of alcohol and water is used as the carrier liquid.

In an ink, the carrier liquid is used in an amount of from about 15% by weight to about 90% by weight, preferably in an amount of from about 30% by weight to about 60% weight of the composition.

Coating compositions to be useful exhibit a desirable balance among viscosity, solubility, compatibility of components, and wettability of the substrate. When the coating composition is an ink useful in printing operations, electro-static ink deposition methods require that resistivity and polarizability also be considered.

Useful polymers for systems in which the carrier liquid is aqueous include, but are not limited to poly (ethylene oxide)s, poly(acrylamide)s, poly(vinylpyrrolidone)s, poly(vinyl alcohol)s and poly(vinyl acetate)s. Included in each of these terms are both homo- and copolymers of the primary monomers, as well as mixtures thereof.

Useful polymers for use in carrier liquids based upon "hydrocarbon solvents" include, but are not limited to cellulosic polymers, poly(alpha-olefins) where the olefins contain six or more carbon atoms when used in conjunction with non-polar solvents such as alkanes; acrylic polymers when used in conjunction with polar organic solvents such as esters, ketones, and glycol- and other ethers. Esters include but are not limited to ethyl acetate, butyl acetate, butyl cellosolve acetate; carbitol esters; ketones include but are not limited to acetone, methylethylketone, diisopropylketone, and cyclohexanone. Ethers include but are not limited to tetrahydrofuran, dioxane, tetrahydrofurfural alcohol, Other useful solvents falling outside these classes include terpineol, toluene, xylene, dimethylformamide, pyridine, ethylbenzene, carbon disulfide, 1-nitropropane, and tributylphosphate.

Mixtures of polymers are also suitable. Mixtures of polymers often provide a more desirable combination of properties than can be obtained from a single polymer.

Preferably the polymer is soluble in the carrier liquid. However, the polymer can be present as a dispersion in the carrier liquid as well.

One fundamental requirement for the polymer employed herein is that the polymer can not exhibit significant absorbance at either the excitation or emission wavelengths of interest because of interference with the intensity of the observed luminescence.

In an ink, the polymer is employed in an amount of from 0% to about 15% by weight of the ink composition, preferably, about 2% to about 10%. Excessive amount of the polymer can adversely affect the viscosity of the ink composition.

For some printing applications, such as xerography and ink jet, electrical resistivity can be an important property. In those applications, the composition of the present invention can further comprise an electrolyte to obtain the desired electrical resistivity of the jet ink composition. Any suitable electrolyte known to those of ordinary skill in the art can be used. Suitable electrolytes include but are not limited to alkali and alkaline earth metal salts such as lithium nitrate, lithium chloride, lithium thiocyanate, sodium chloride, potassium chloride, potassium bromide, calcium chloride, and the like, and amine salts such as ammonium nitrate, ammonium chloride, dimethylamine hydrochloride, hydroxylamine hydrochloride, and the like. It is important that the electrolyte salt not interfere with the luminescence.

The electrolyte is preferably present in the ink composition in the range of from about 0.1% to about 2%, more preferably 0.4% to 0.6%, by weight of the ink composition.

The composition of the present invention can further comprise a pH adjusting agent if needed to enhance the dissolution of the binder resin, or improve compatibility with the surface. The desired pH will be dependent upon the particular solvent used and also to some extent upon the other components employed. Any suitable pH adjusting agent, acid or base, can be used so as to maintain the pH of the ink composition in the range of from about 4.0 to about 8.0, preferably in the range of from about 4.5 to about 7.5.

The ink can further comprise a humectant when the liquid is water in order to prevent drying of the ink during the printing operation, as well as during storage of the ink. Humectants are hydrophilic solvents preferably having boiling points in the range of from about 150° C. to about 250° C. Any suitable humectant known to those of ordinary skill in the art can be used. Examples of suitable humectants include glycols such as ethylene glycol, propylene glycol, glycerin, diglycerin, diethylene glycol, and the like, glycol ethers such as ethylene glycol dimethyl ether, ethylene glycol diethylether, cellosolve, diethylene glycol monoethylether (Carbitol), diethylene glycol dimethylether, and diethylene glycol diethylether, dialkylsulfoxides such as dimethylsulfoxide, and other solvents such as sulfolane, N-methylpyrrolidinone, and the like. Preferred humectants include propylene glycol and diethyleneglycol monoethylether.

Any suitable amount of the humectant can be used, preferably in an amount of from about 0.5% by weight to about 5% by weight of the ink composition, and more preferably in the amount of from about 1% by weight to about 3% by weight of the ink composition. Excessive use of the humectant is to be avoided because it will increase the toxicity and/or the viscosity of the ink.

The ink can further comprise a suitable biocide to prevent growth of bacteria, mold or fungus. Any suitable biocide can be used. DOWICIL™ 150, 200, and 75, benzoate salts, sorbate salts, and the like, methyl p-hydroxybenzoate, and 6-acetoxy-2,2-dimethyl-1,3-dioxane are examples of suitable biocides. The biocide can be present in the ink of the instant invention in the range of from about 0.05% by weight to about 0.5% by weight, preferably in the amount of from about 0.1% by weight of to about 0.3% by weight of the jet ink composition.

The ink can further comprise a defoamer to prevent foaming of the ink during its preparation, as well as during the printing operation. Any suitable defoamer known to those of ordinary skill in the art can be used, preferably those that are miscible with the liquid. Suitable defoamers include silicone defoamers and acetylenic defoamers. The amount used is preferably in the range of from about 0.01% by weight to about 1% by weight of the ink composition, and more preferably in the range of from about 0.05% by weight to about 0.35% by weight of the ink composition. The weight percentages given above refer to that of the active ingredient, and if the defoamer is sold in a diluted form, the amount of the diluted defoamer used will be proportionately increased. Excessive use of the defoamers is to be avoided because it can adversely affect the print quality such as adhesion to the coated substrate.

The ink can be printed on any suitable substrate including papers, including coated papers, plastics, leather goods, fabrics, polymeric films, glass, ceramics, metals, and so forth.

To prepare an ink suitable for use in this invention, the particulate luminescent composition can be dispersed in the carrier liquid using a media mill, sand mill, high speed disperser, mulling plates or other means known in the art. The dispersion so produced should contain 10%-70% by weight, preferably 40%-60% by weight, of the particulate luminescent composition. A dispersing aid can be added equal to ½ to ¹⁄₁₀, preferably ¼ to ⅕, the weight of the particles, and the remainder should be the liquid carrier or mixture of suitable liquids.

When milling or mulling, dispersion and comminution occur simultaneously.

In general, a preferred ink formulation is prepared by combining a liquid carrier, a polymeric binder soluble therein, and the particulate luminescent composition so that the resulting composition contains 10-70% by weight, preferably 40-60%, of the particles, 0-15% by weight, preferably 2-10%, of polymer dissolved in the solvent, and 15-90%, preferably 30-60% by weight of the carrier liquid. Optionally the composition can contain plasticizer of 0 to 5% and dispersant of 0 to 8%. The ingredients can be combined in any order. The polymer can first be dissolved in the solvent followed by addition of the particulate material which is then dispersed therein; the particulate material so added can be in the form of dry particles or a pre-prepared particle dispersion. Alternatively, the particle dispersion can be prepared first followed by addition and dissolution of the polymer.

Varnishes according to the present invention may be formulated by adapting conventional methods known in the art. In a typical formulation, the particulate luminescent compound is combined in a viscous polymer solution consisting of ca. 10% of a fugitive solvent. Varnishes are conventionally applied by brushing, rolling, and spraying.

According to the present invention, a method is provided wherein the luminescent coating on the surface of the coated article is subject to UV illumination at one or more preselected wavelengths and stimulated thereby to luminance. The ratio of pre-selected intensity peaks is determined and compared to the standard described supra. Depending upon whether it is determined to match or not match the standard, the coated article is subject to being classified as authentic or inauthentic, respectively.

The specific instrumentation by which the illumination is provided and the relative intensity of the pre-selected luminescence peaks is determined is not critical to the operability of the invention. One method, as described in the specific embodiments infra is to employ well-known laboratory phosphorimeters or spectrometers, in conjunction with laser light sources, filtered broad band sources, and other sources of illumination well-known in the art of spectroscopy.

Alternatively, an electro-optical reader can be employed for reading an identifying mark as herein described, which comprises a source of light directed towards the mark to illuminate at least a portion of it, a photo-detector means for detecting the luminescence obtained from the illuminated portion of the mark, and a determining means connected with the photo-detector for comparing an output from the photo-detector with a reference signal stored therein to verify the authenticity of the mark. One instrument satisfactory for use in the method of the present invention is the electro-optical reader in Inaba et al., U.S. Pat. No. 6,981,648.

A suitable such electro-optical reader comprises a UV laser oscillator or light emitting diode the light from which is shaped into a fine pencil by a condensing lens. The pencil of laser light emerging from the optical illumination system is directed to the surface of the coating herein described. The luminescence stimulated thereby passes to a photo-detector in the electro optical reader after having passed through a plurality of optical filters operable to permit passage therethrough of only light of the predetermined wavelengths of the luminescence intensity peaks of interest. The photo-detector can be a photodiode, an avalanche photodiode or any other high sensitivity photo-detector. An output signal from the photo-detector array contains the intensity data of the preselected intensity peaks. The photodetector signals can be amplified and conditioned as necessary, and the signals are combined to provide the intensity ratios thereof. The resulting ratio is then supplied to a determining circuit which includes a memory in which the standard as described supra. The determining circuit can be electrically connected with a display unit allowing the result to be visually indicated.

In a further embodiment, the present invention provides a method comprising, within a first time period, a coater causing to be disposed upon the surface of a first plurality of articles, a first luminescent coating, thereby producing a first plurality of coated articles; and, within a second time period, the coater causing to be disposed upon the surface of a second plurality of articles, a second luminescent coating, thereby producing a second plurality of coated articles; a classifier causing to be exposed at least a portion of one or more of the first or second plurality of coated articles to ultraviolet light at one or more preselected wavelengths thereby causing the coating to exhibit, respectively a first or second luminescence spectrum, each the first or second luminescence spectrum exhibiting a plurality of intensity peaks the wavelengths of the peaks having been predetermined using light comprising the preselected wavelength or wavelengths to create a first standard corresponding to the first plurality of coated articles and a second standard corresponding to the second plurality of coated articles; determining the peak intensity ratio of at least two the intensity peaks in the first or second luminescence spectrum of the first or second coating; comparing the peak intensity ratio so determined with, respectively, the first or second standard depending upon whether the coated article is from the first or second plurality of coated articles; and, classifying the article according to whether or not the peak intensity ratio does or does not match the first or second standard, respectively; each the coating comprising a particulate luminescent composition dispersed therein.

The method of the present invention provides a means for a first party, the "coater," to provide a luminescent identifying mark comprising the particulate luminescent composition described supra on a plurality of objects, and for a second party, "the classifier," to compare the luminescence of the identifying mark on objects received by the classifier to the standard provided to the classifier by the coater. In this manner, the classifier can determine whether the object the luminescent coating of which is being inquired of is authentic or not.

The method further provides for the coater to change the luminescent coating deposited upon the plurality of objects after some period of time from one particular particulate luminescent composition to another, thereby changing the standard as well. By providing the new standard to the classifier, the coater can then make whatever change desired in the coating of the plurality of objects.

In particular, it is envisioned that the coater may be a manufacturer or distributor of manufactured articles. In order to combat the presence of counterfeit goods in the marketplace, the coater applies a coating comprising a first embodiment of the particulate luminescent composition as described, supra. The coating so formulated is then applied to the manufactured articles for a period of time. After that period of time, which may be of any arbitrary length, the coater changes to a different coating composition comprising a second, and different, particulate luminescent composition. As described supra, the second particulate luminescent composition will exhibit a difference in peak intensity ratios, or, indeed, different intensity peaks altogether, from those of the first particulate luminescent composition. Therefore the standard as defined supra will also be changed from a first standard to a second standard. By informing the classifier of the change in standard, the coater can then readily change from one identifier to a different identifier.

The coater may provide the carrier information concerning the appropriate standard to employ by any means available in the art, both involving the transfer of written documents, or the transmission of electronic signals to an automated detection apparatus.

EXAMPLES

General Method

Luminescence Spectra

The data are collected with a SPEX JY spectrofluorimeter equipped with the phosphorimeter option. The excitation wavelength is 394 nm (10 nm bandpass) and the pulsewidth is nominally 80 microseconds. Spectra are collected at 5 nm resolution with a 0.1 msec time delay after the excitation pulse to permit background fluorescence from the label substrates to decay. A 405 nm long-pass filter is used before the emission monochromator to eliminate second-order excitation light. Each spectrum is the average of 150 scans, each collected with one excitation pulse per 1 nm wavelength step. The detection time window is 10 msec.

Example 1

2.177 g of $CaCl_2.2H_2O$ (Sigma-Aldrich, 99.9%), 11.838 g of $SrCl_2.6H_2O$ (Sigma-Aldrich, 99.9%) and 0.44 g of $EuCl_3.6H_2O$ (Sigma-Aldrich, 99.9%) were stirred into 150 ml of deionized water in a polycarbonate Erlenmeyer flask for about 5 minutes to ensure dissolution of the solids.

Separately, 4.489 g of $NH_4F$ (Alfa Aesar, ASC reagent 99%) was dissolved by stirring into a further 150 ml aliquot of deionized water for about 5 minutes to ensure dissolution of the solids.

The prepared solutions were simultaneously but separately fed by a peristaltic pump at 10 ml/min through silicone rubber tubing into the two arms of a plastic tee (T). Teflon® tubing ran from the leg or output branch of the T into the product flask. A precipitate formed within the output branch of the T immediately beyond the point at which the two streams merged, forming a suspension in the water. The suspension formed was discharged into the product flask. During the discharge the flask containing the product suspension was stirred by magnetic stirring. After discharge was complete, the suspension was held static for about 24 hrs at ambient temperature. The resulting suspension was then centrifuged (Sorvall RC5C, Thermo Electron Corp.) at a relative centrifugal force of 9500×g for 40 min, and the supernatant (containing soluble salts) decanted and discarded. The residue was redispersed in a fresh aliquot of about 300 ml of deionized water using ultrasonic agitation (Sonics and Materials, Inc, Danbury, Conn.) at 50 W/cm². The resulting dispersion was again centrifuged and the supernatant again decanted and discarded.

The washed as precipitated powder residue was dried in a laboratory drying oven at 60° C. in air for 24 hrs to form about 15 g of a dry powder compact The oven dried powder compact was then hand-ground in a mortar and pestle to from a uniform dry powder.

A 15 g aliquot of each of the washed as precipitated powders was redispersed in about 100 ml of deionized water using ultrasonic agitation. The washed 100 ml suspension was placed in a 100 ml screw cap flexible-walled Teflon® bottle. The bottle was filled right to the brim before placing the cap on in order to exclude air. The Teflon® container containing the suspension was placed in a stainless steel pressure reactor (filled with water) and heated for 6 hrs at 245° C. at a saturated vapor pressure of 568 psi. The resulting hydrothermally treated suspension was then centrifuged and decanted as described above. The wet powder residue was dried in a laboratory drying oven at 60° C. in air for 24 hrs to form a dry powder compact. The oven dried powder compact was then hand-ground in a mortar and pestle to from a uniform dry powder.

The fired powder is hand ground using a mortar and pestle, then placed into a ceramic jar mill with ½" milling media. Isopropyl alcohol is added to fill the mill to approx. ⅔ full. The slurry is milled overnight. The milled slurry is placed into a disposable filter and the isopropyl alcohol is filtered off leaving the milled particles in the filter. The particles are air dried for 8 hrs. then placed in a 70 C oven to complete the drying process overnight.

Approximately 1.5 g of the powder: as prepared is combined with approximately 1 g of a solution of 10% ethyl cellulose and 90% 1-methyl-4-(1-methylvinyl)cyclohexanol (β-terpineol) on the bottom glass plate of a model M-5 Hoover Auto Muller (Hoover Color Corp., Irvingto, N.J.). Two pressure weight plates provided therewith are set in place over the combination and locked into place. Twenty rotations are performed after which the sample is re-spread on the glass plate using a spatula. 4-5 more cycles of twenty rotations are performed, in between each, the sample is re-spread with the spatula. The final product is a highly viscous paste.

The prepared paste is screen-printed onto a commercially available Ink Jet Label (Avery Dennison Corp.) label stock using a 325 mesh screen in a Series L-400 screen printer (Engineered Technical Products, Somerville, N.J.). Three coats are applied to the label, to yield a coating weight of approximately 3-6 mg/cm² of the particulate luminescent composition in the screen-printed film. The film is heated to 110-125° C. for 10 minutes to evaporate any residual solvent.

The luminescence intensity ratio is then measured for the 589 nm and 610 nm emission lines for all 6 films as described supra, and is found to be 2.60

Example 2

The preparative method and materials of Examples 1-6 are repeated except that after the second ultrasonically-driven redispersion the resulting suspension is not dried, but rather the resulting suspension is placed into a Teflon® PFA container which in turn is placed into a pressure vessel, and heated to 245° C. for 6 hrs. After the heating the suspension is filtered through a 1.0 um syringe filter. The filtrate is redispersed in deionized water resulting in a suspension that is 5.73 wt. % solids.

The suspension so prepared is ink jetted as 2 cm×2 cm squares onto the surface of a paper or of a Mylar® (DuPont-Teijin Films, Wilmington, Del.) film using a Jetlab II Table-Top Printing Platform (Microfab Technologies, Inc. Plano, Tex.) equipped with a 50 micron nozzle and 1 mm work distance. A single coating layer consumed 0.5 microliters/cm² which at 5.73% solids comes to a dry weight of 29.8 mircrograms/cm². As indicated in Table 3, coatings of up to 18 coats are prepared. The luminescence intensity ratios determined as described supra for peaks at 589 nm, and 610 nm are found to be in the range of 2.60±5%.

TABLE 3

| | Ink-jetted samples | | |
|---|---|---|---|
| Example | Number layers | 2% Eu CaF2 (mg/cm2) | Substrate |
| 10 | 12 | 0.3578 | paper |
| 11 | 15 | 0.4470 | paper |
| 12 | 18 | 0.5364 | paper |
| 13 | 15 | 0.4470 | Mylar ® |
| 14 | 12 | 0.3578 | Mylar ® |

What is claimed is:

1. A method comprising exposing at least a portion of a luminescent coating disposed on a surface of an article to ultraviolet light at one or more preselected wavelengths causing said luminescent coating to exhibit a luminescence spectrum wherein the luminescence spectrum exhibits a plurality of intensity peaks that have been predetermined to create a standard; determining the intensity of at least two peaks in the luminescence spectrum of the coating; determining a peak intensity ratio of at least two peaks; comparing the peak intensity ratio thereby determined with the standard; and, classifying the article according to whether or not the peak intensity ratio does or does not match the standard; wherein the luminescent coating comprises a particulate luminescent composition comprising a rare-earth-doped solid-state solution of alkaline earth fluorides represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a, b, and c are not equal to zero; the particulate luminescent composition exhibiting a luminescence spectrum having a plurality of intensity peaks at characteristic wavelengths.

2. A method comprising within a first time period, a coater causing to be disposed upon the surface of a first plurality of articles a first luminescent coating producing a first plurality of coated articles; and, within a second time period, the coater causing to be disposed upon the surface of a second plurality of articles a second luminescent coating, thereby producing a second plurality of coated articles; a classifier causing to be exposed at least a portion of one or more of the first or second plurality of coated articles to ultraviolet light at one or more preselected wavelengths thereby causing the coating to exhibit, respectively a first or second luminescence spectrum, each said first or second luminescence spectrum exhibiting a plurality of intensity peaks the wavelengths of the peaks having been predetermined using light comprising the preselected wavelength or wavelengths to create a first standard corresponding to the first plurality of coated articles and a second standard corresponding to the second plurality of coated articles; determining the peak intensity ratio of at least two intensity peaks in the first or second luminescence spectrum of the first or second coating; comparing the peak intensity ratio so determined with, respectively, the first or second standard depending upon whether the coated article is from the first or second plurality of coated articles; and, classifying the article according to whether or not the peak intensity ratio does or does not match the first or second standard, respectively; each said coating comprising a particulate luminescent composition, the particulate luminescent composition comprising a rare-earth-doped solid-state solution of alkaline earth fluorides represented by the chemical formula $$RE_x(Ca_aSr_bBa_c)_{1-x}F_{2+x-2y}O_y$$

wherein RE represents a three-valent rare-earth element, $0.005 \leq x \leq 0.20$, and $0 \leq y \leq 0.2$, $a+b+c=1$, with the proviso at least two of a, b, and c are not equal to zero; the particulate luminescent composition exhibiting a luminescence spectrum having a plurality of intensity peaks at characteristic wavelengths.

3. The method of claim 1 wherein at least one pair of the plurality of peaks exhibits an intensity ratio with respect to one another that differs by at least 5% from the corresponding peak intensity ratio of the corresponding reference composition.

4. The method of claim 2 wherein at least one pair of the plurality of peaks exhibits an intensity ratio with respect to one another that differs by at least 5% from the corresponding peak intensity ratio of the corresponding reference composition.

5. The method of claim 1 wherein the coating further comprises a polymer.

6. The method of claim 2 wherein the first coating and the second coating further comprise a polymer.

7. The method of claim 1 wherein RE is $Eu^{+3}$, $Tb^{+3}$ or $Er^{+3}$.

8. The method of claim 2 wherein RE is $Eu^{+3}$, $Tb^{+3}$ or $Er^{+3}$.

9. The method of claim 1 wherein c=0.

10. The method of claim 2 wherein c=0.

11. The method of claim 1 wherein $0.01 \leq x \leq 0.10$.

12. The method of claim 2 wherein $0.01 \leq x \leq 0.10$.

13. The method of claim 3 wherein the intensity ratios differ by at least 10%.

14. The method of claim 4 wherein the intensity ratios differ by at least 10%.

15. The method of claim 5 wherein the polymer is ethyl cellulose.

16. The method of claim 6 wherein the polymer is ethyl cellulose.

* * * * *